United States Patent
Berlin et al.

(10) Patent No.: US 6,459,477 B1
(45) Date of Patent: Oct. 1, 2002

(54) METHOD AND DEVICE FOR MEASURING PAINTED TEST TABLES

(75) Inventors: Harald Berlin, Nottuln; Bernd Biallas, Albersloh; Wolfgang Duschek; Werner Rotz, both of Münster, all of (DE)

(73) Assignee: BASF Coatings AG, Muenster-Hiltup (DE)

( * ) Notice: Subject to any disclaimer, the term of this patent is extended or adjusted under 35 U.S.C. 154(b) by 0 days.

(21) Appl. No.: 09/269,418

(22) PCT Filed: Sep. 12, 1997

(86) PCT No.: PCT/EP97/05005

§ 371 (c)(1),
(2), (4) Date: May 19, 1999

(87) PCT Pub. No.: WO98/14778

PCT Pub. Date: Apr. 9, 1998

(30) Foreign Application Priority Data

Sep. 30, 1996 (DE) ............................. 196 40 376

(51) Int. Cl.[7] ........................ B07C 5/10; G01N 21/86; G01N 11/30; G01N 11/06
(52) U.S. Cl. .................. 356/73; 356/630; 356/625; 250/559.27; 250/559.29; 250/559.33; 209/576
(58) Field of Search ................. 356/371, 381, 356/445, 446, 73; 250/559.27, 559.29, 559.33, 223 R; 209/381, 580, 576, 577

(56) References Cited

U.S. PATENT DOCUMENTS

| | | | |
|---|---|---|---|
| 4,561,776 A | 12/1985 | Pryor | |
| 4,615,902 A | 10/1986 | Falcoff et al. | |
| 4,686,374 A | * 8/1987 | Liptay-Wagner et al. | ..... 356/36 |
| 4,920,385 A | 4/1990 | Clarke et al. | |
| 5,062,298 A | 11/1991 | Falcoff et al. | |
| 5,452,078 A | * 9/1995 | Cheng | ......... 356/400 |
| 5,550,632 A | 8/1996 | Harata | |
| 5,619,319 A | 4/1997 | Muraoka | |

FOREIGN PATENT DOCUMENTS

EP 0 383 322 2/1990 .......... G01N/35/00

OTHER PUBLICATIONS

Valcarcel et al.: Automatic Methods of Analysis. Techniques and instrumentation in Analytical Chemistry vol. 9 1988, Elsevier Amsterdam NL XP002051739, pp. 249–272.

Valcarcel et al.: "Automatic Methods of Analysis. Techniques and Instrumentation in Analytical Chemistry vol. 9", pp. 249–272.

* cited by examiner

*Primary Examiner*—F. L. Evans
*Assistant Examiner*—Zandra Smith

(57) ABSTRACT

Apparatus and method for measuring coated test panels, the test panels (2) being taken from a feed magazine (1) by a gripping and moving device, e.g. a laboratory robot, placed on a measuring station (9) and, finally, transferred to a delivery station (5). In the measuring station (9) measurement of the various properties of the coating is carried out by the laboratory robot (3) using various measuring devices (4). This process can in particular involve spatial resolution and electronic recording. The test panels can furthermore be distinguished by a bar code system which is recorded and evaluated electronically.

19 Claims, 1 Drawing Sheet

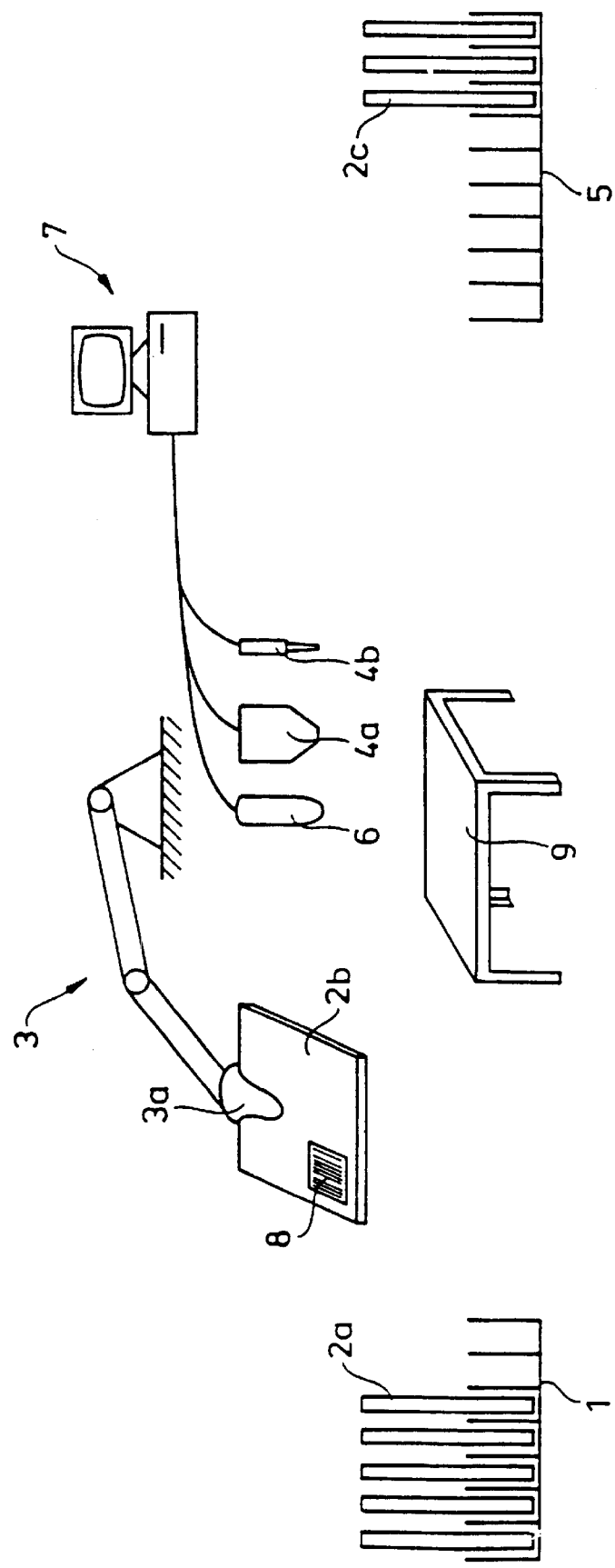

METHOD AND DEVICE FOR MEASURING PAINTED TEST TABLES

BACKGROUND OF THE INVENTION

The present invention relates to a method and an apparatus for measuring coated test panels.

For the development and quality control of coatings and painting materials, it is necessary to investigate the coatings that can be achieved therewith for various properties. For this purpose, as a rule sample coatings are produced, for which the description "test panels" has been adopted, since the article coated in the manner of a sample is often plate-shaped.

However, there are also "test panels" which are curved to different extents, for example when parts of car bodies are used or if it is precisely the coating properties in zones of curvature that are to be investigated.

The properties investigated with the aid of test panels relate to a broad spectrum of relevant properties of the coating. These include, on the one hand, the optical properties and in this case, in particular, the color properties of the coating (color, gloss, leveling, special-effect properties, haze, hiding power). On the other hand, the mechanical properties are of interest, for example such as the hardness of the coating, adhesion to the substrate and elasticity. Finally, further physical properties are of interest, such as the diffusion power of foreign substances in the layer, the electrical conductivity of the layer, the UV absorption capacity, the flame-protection effect and the durability of the layer under practical stresses. Depending on the specific task of the coating, further relevant parameters may be added. On the other hand, it may be the case that not all of the properties listed are of special significance for a specific coating or painting material, but rather that attention can be directed to a few properties.

Hitherto it has been usual to carry out the examination of test panels manually with the aid of suitable measuring devices. To this end, in the laboratory each individual test panel is examined by a worker using the appropriate measuring devices for the properties, and the measurement results are as a rule noted by hand for further evaluation. This procedure is not only very time-consuming, but furthermore is also susceptible to interference and subject to systematic errors. Thus, carrying out the measurements depends, for example, on the habits and the skill of the tester, and on account of the effort, only a few measurements, as a rule only one measurement, take place in relation to each property. Since many coating properties depend interactively (functionally) on one another, for example the hardness on the film thickness, it would be particularly important to carry out the measurements as far as possible under identical conditions, in particular at the same location on the test panel. However, in the case of the previous procedure, this is not ensured since in the case of the manual tests as a rule no attention is paid to the location of the test panel at which the measurement is carried out, and since such a location is also not able to be determined reproducible by hand with the necessary precision. The measuring methods previously used are thus time-consuming and, furthermore, subject to high errors. Finally, in the case of carrying out the tests manually, confusion may also occur if measurement data are inadvertently allocated to the wrong test panel.

An automatic measuring device is described in EP-0 383 322 A2 for biochemical analyses. In the case of this device, indicator preparations on object carriers from a supply are gripped and guided along a fixed path through the measuring device, which they finally leave at an ejection station. On their way, the indicator preparations have added to them the sample liquid to be examined, and any optical or electrochemical changes which set in are measured by an appropriate sensor. A measuring device of this type, or a comparable automatic measuring device would, however, be incapable of application or disadvantageous in the case of measuring coated test panels, since it requires a fixed geometrical format of the test panels, contains only one single type of sensor and, in particular, cannot use the (manual) measuring devices which are. usual and available.

By contrast, the object of the present invention was to provide a method and an apparatus which do not have the disadvantages outlined. The measurement of test panels is therefore to be simplified considerably and at the same time possible with higher precision and reproducibility. The method is intended to be able to change without difficulties and flexibly between various test-panel geometries and the measurements of different properties, and allocates the measurement results reliably to the measured test panels, it being in particular intended for spatially resolved measurements also to be possible. The measurements themselves are intended to be carried out with various measuring devices on a sample in a spatially resolved manner, that is to say highly precise measurements at the same-location. Furthermore, it is intended to be able to use available (manual) measuring devices.

SUMMARY OF THE INVENTION

This object is achieved by a method which comprises the following steps:

a) depositing the coated test panels in a feed station, b) transferring a test panel from the feed station to a measuring station by means of a gripping and moving device, c) gripping the measuring devices by means of the gripping and moving device and carrying out the measurements on the test panel in the measuring station, d) transferring the measured test panel into a delivery station by means of the gripping and moving device.

BRIEF DESCRIPTION OF THE DRAWINGS

The FIGURE is a schematic diagram of one embodiment of the invention.

DETAILED DESCRIPTION OF THE INVENTION

Using the method according to the invention, the measurement of the test panels proceeds completely automatically following their production. The necessary processing and movement steps are carried out by means of a gripping and moving device ("manipulator"). This is suited in particular for gripping the various measuring devices, for guiding the various measuring devices to the test panel, for carrying out the measurement on the test panel and finally for placing the measuring device once more at the original location. In this case, because the measuring process is carried out by a machine, it is ensured in particular that precisely known locations on the test panel can be moved to and measured. In particular, in this case the measurement of all the properties can take place at the same location, so that a correct correlation of the properties with one another is produced. This was not ensured in the case of the method previously carried out manually. If, for example, film hardness or color covering power are measured at a location that differs from that of the film thickness, these properties cannot be correlated and the actually present interactive relationships are not observed. In the case of the method according to the invention, on the other hand, all the measurements are carried out at the same location. This increases the precision of the result, since interactive relationships between the properties which are known from practice or theory can be utilized in order to match the respective measured values amongst one another. As a result of the ability to display the functional relationship between various measured variables, it is even possible for completely new properties to be ascertained in addition to the previously recorded values, for example the hiding power in oblique view or clouding in oblique view. Furthermore, using the method according to the invention, the precision of the measurement can be increased, in that all the properties are determined many times, preferably at different locations on the test panel. Because the method is carried out fully automatically, such multiple measurements are not associated with increased personal effort. If required, measurements of this type can also be carried out outside the usual working time, for example during the night. With the aid of the measurement results, which are available many times, it is then possible on the one hand to carry out a statistical evaluation of the result, which leads to increased precision, on the other hand the properties are correlated with the measurement location on the test panel. A spatially resolved measurement of this type supplies further valuable indications as to the properties of the coating of the test panel.

The method according to the invention is extremely flexible with regard to the number and type of measuring devices used, and by means of appropriate programming of the control system of the gripping and moving device, it is in particular also possible for the conventional manual measuring devices now to be used in automatic operation. Furthermore, the method is also flexible in relation to the test panels measured. These may be of different size and shape, in particular have different curvatures. As a result of the fact that the measuring devices are gripped and guided by the gripping and moving device, they can in particular also be moved on freely predefinable paths, so that in particular measurements along curved surfaces are possible.

The free mobility of the gripping and moving device also has the advantage that it makes a compact arrangement of the measuring devices and test objects possible.

In a development of the method according to the invention, the measurement data obtained with the aid of the measuring devices are recorded, stored, evaluated and displayed electronically. The electronic recording of the measurement data in a central unit considerably facilitates overseeing and further processing the data obtained.

The automatic processing of the test panels can be rounded off further by
a) the test panels, before their introduction into the feed station, being provided with a machinereadable identifier which contains information relating to the identification and hence the test plan,
b) the machine-readable identifier being recorded automatically and the information contained therein being accepted into the control system of the gripping and moving device and/or the data acquisition system.

The machine-readable identifier is preferably a bar code system, which can be applied to the test panels with the aid of suitable stickers.

Identification of the test panels in this way has the advantage that all the relevant information is directly linked with the test panel itself. It is therefore no longer possible for confusions to arise, in which, for example, a test panel is wrongly measured or the measurement results obtained are allocated to a different test panel. Furthermore, it is not strictly necessary to pay attention to the sequence of the test panels within the feed station, since the test panels are not identified by their position within the series of the panels to be measured. In particular, this flexibility also allows different users to produce test panels and feed them to the measuring method. Each individual user needs only to provide his test panel with the appropriate identifiers, and does not need to worry about specific rules when depositing the test panels. Likewise, an automatic allocation of the test panels to various users of the measuring system can be performed in the feed station. Finally, the identifier may also contain information about the shape and size of the test panel. This makes the processing of various types of test panel easier, since their shape/size no longer has to be established by other sensors.

The method according to the invention is preferably employed in order to measure film thickness, leveling, color, the color coordinates L (lightness), a (red-green), b (yellow-blue), hardness, haze and/or gloss of the test panels. However, it is also possible to measure other properties (for example scratch resistance, freedom from tack, wetting stability, surface topography). For this purpose, it is only necessary to provide an appropriate measuring device, which can be operated by the gripping and moving device. The determination of color properties is of special significance here. Detailed and comprehensive information about the color is necessary for some testing tasks, for example the determination of clouding in metallic coatings or the determination of the color stability of top coats. For such measurement tasks it is of advantage to use a color measuring device which supplies the color coordinates L, a, b. It is very particularly advantageous if these color values are ascertained at different angles of observation, preferably at 20°–30°, 40°–50° and 70°–80°, very particularly preferably at 25°, 45° and 75°.

Furthermore, by means of correlation or the observation of the functional relationship, completely new properties may be ascertained from the various measured variables which are obtained with the method according to the invention, for example the hiding power or clouding in oblique view at 75°.

In order that the measuring devices used in the method according to the invention supply precise data, it is necessary to subject them to a test means monitoring/calibration at specific intervals. In this case, it proves to be a problem that the measuring devices have to be dismantled and calibrated off-line, so to speak. This is awkward, costs time and is subject to errors, since the procedure can also be forgotten. The method according to the invention therefore also includes an automatic calibration of the measuring devices. In this case, appropriate programming of the gripping and moving device ensures that the latter automatically carries out the predefined calibration in relation to time, type of calibration and documentation. For this purpose, the gripping and moving device has access at all times to the standards which it needs for the calibration of the measuring devices and which are arranged in its sphere of activity. The calibration can be performed as a rule such that a reference measurement is performed with the aid of the standard (instead of the test panel).

The invention also includes an apparatus for measuring coated test panels, which contains the following elements:

a) a feed station for the test panels to be measured,
b) a gripping and moving device for the movement of the test panels and their measurement using measuring devices,
c) at least one measuring device, with which the coating properties of interest of the test panel can be measured,
d) a delivery station for the measured test panels.

Using the apparatus according to the invention, it is in particular possible for the method according to the invention and outlined above to be carried out. In this case, the centerpiece is the gripping and moving device (manipulator), with the aid of which the entire measuring operation can proceed completely automatically. An apparatus of this type can in particular be a laboratory robot, that is to say an apparatus which is permanently installed, has a gripper arm with at least one articulation and one gripping apparatus, and which can carry out movement sequences that are programmed in or guided in advance. Using such an automatic measurement of the test panels, it is possible not only for the personal effort to be reduced considerably, but also for higher precision and reliability of the measurement results to be achieved. This is brought about, on the one hand, by the fact that a plurality of measurements of the same property can be made without problems and can then be evaluated statistically, on the other hand by the fact that the respective measurements are correlated precisely with one measurement location and are thus more reliable and can also be matched to one another.

Furthermore, the apparatus according to the invention preferably contains a reading device for the electronic recording of identifying data from test panels. In this case, it can preferably be a barcode reader. The recording of the barcode can be performed in such a way that the test panel with the barcode sticker is guided past the reading device, or conversely the gripping and moving device grips the reading device and passes it by the stationary test panel. In the case of the last variant, the recording of the barcode in principle progresses in a manner similar to the measurement of the other coating properties. Conversely, within the scope of the invention, it is also conceivable for the measurements that the test panel is guided along the stationary measuring devices and the measurement is performed at the same time.

Within the apparatus according to the invention, the measuring devices and/or the reading device of the identifier, if present, are connected to an electronic data processing system. In this case, this may be, for example, a normal personal computer PC, which has appropriate electronics for the recording and, if necessary, digitizing of measurement data. The automation of the apparatus is rounded off by: electronic recording of this type. The measured values obtained are stored and evaluated directly in the electronic central unit. Furthermore, this electronic central unit can also undertake the control of the gripping and moving device. This is particularly expedient when it obtains the electronically recorded identifying data from the test panel and, depending on this data, forwards the measuring program to be used (measuring devices to be gripped, positions to be moved to on the test panel, . . . ) to the gripping and moving device.

The feed station and/or delivery station within the apparatus according to the invention are preferably equipped as magazines for the test panels. Magazines of this type can be loaded with test panels outside the apparatus and then, within the apparatus, ensure that the test panels are situated at defined locations and can thus be easily and reliably found by the automatic gripper. Furthermore, different units of the laboratory may have and fill their own magazine in each case, with the result that the allocation of the test panels is optimized in organizational terms.

In this case, the magazines can in particular be designed in such a way that they can accommodate test panels of different size and shape. In this case, the different measuring programs, tailor-made to different panel sizes and geometries, are stored in the control system of the gripping and moving device.

Within the apparatus according to the invention, different measuring devices can be used. The only condition is that these can be moved and operated by the gripping and moving device. In this case, it is in particular also possible to keep the measuring devices ready at standardized places, so that they can easily be exchanged for one another, or that new measuring devices can be inserted into the apparatus. In this case, only an adaptation of the gripping and moving device is necessary, in that the latter also finds and correctly operates a new device. The measuring devices that can be used within the scope of the apparatus according to the invention are, in particular, measuring devices for film thickness, leveling, color, haze and gloss, as well as for scanning the topography (perthometer) of the test panels. However, as already mentioned, the apparatus is not restricted to these measuring devices.

The invention is explained by way of example in the following text with the aid of the figure.

The figure shows one implementation of the apparatus according to the invention having various elements. The coated test panels 2, following their production, are firstly deposited in the feed station 1. In the figure, the feed station 1 is implemented as a magazine, into which the test panels 2a are inserted.

A gripping and moving device 3 then grips the test panels 2a from the magazine 1, in order to feed them to the measurement. The gripping and moving device can, in particular, be configured as a laboratory robot system 3, for example a 5-axis robot (such as "MOVEMASTER RV-E2/E3J" from Mitsubishi Electric, Ratingen). The test panel 2b, held with the aid of the gripper 3a, is then transferred from the receiving station 1 to a measuring station 9. The measuring station 9 may, in particular, be a measuring table, on which the test panel is adequately fixed and aligned. In this case, the fixing of the test panel can be performed by suitable stops at the edge of the table, or by adequate frictional forces between substrate and sample or using a holding device based on vacuum (sucker).

The test panels 2 also have a sticker with a barcode 8. By means of this barcode (other types of encoding are also conceivable, provided they are machine-readable), important information about the test panel is reproduced. This can be, for example, the producer of the panel, production process, coating material, desired measurement, locations of the measurement and so on. The barcode sticker 8 can be detected with the aid of an automatic reading device 6. The test panels located on the measuring station 9 are finally measured with respect to the desired properties. To this end, the robot 3 grips the measuring devices 4a, 4b one after another and guides them to the desired points on the test panel 2. Examples of suitable measuring devices are magneto-inductive or eddy-current film thickness measuring devices (e.g. MINITEST devices from the firm Elektro-Physik, Cologne, Germany), goniospectrometers (e.g. X-Rite® MA68) or gloss measuring devices (e.g. micro-TRI-gloss, wave-scan plus or mirror-TRI-gloss from the firm BYK-Gardner, Geretsreid, Germany), Perthometer from the Mahr company. Here, the precise measurement locations can vary from panel to panel. By means of multiple measurement at one location, or by means of measurements at various locations, more comprehensive information about the coating can be obtained than is possible in the case of the usual manual measuring method. In particular, it is hence also possible to correlate the measurements of various properties with one another. The measuring devices 4 and the reading device 6 are connected via appropriate lines to a central data acquisition unit, a personal computer 7. The data can be digitized either still inside the measuring device or inside the PC 7.

After the measurements have been completed, the robot 3 grips the test panel on the measuring station and transfers this into the delivery station 5. This may again be a magazine, into which the test panels are inserted in sequence. It is likewise possible to provide a plurality of magazines in parallel alongside one another, the robot 3 undertaking an allocation of the test panels into the various magazines in accordance with the information on the coding 8.

In trials, the method according to the invention was used for assessing clouding. A coating which tends to clouding was compared with a coating which exhibits no clouding. In each case, the lightness of the coating film was measured at different film thicknesses using a basic coating film applied in a wedge shape (5–20 $\mu$m). The evaluation in relation to the curves of lightness at 25° angle of observation showed no difference in the formulations, although they are visually distinctly perceived. Only a change of the angle of observation to 45° and/or 75° shows the clear differences in the formulations. This result documents the necessity of complete measurement data determination, for example, as in the trial illustrated, at various angles of observation. Using the method according to the invention, operating completely automatically, this is rapidly and precisely possible, whereas in the case of the conventional manual measuring methods, only an inadequate minimum program could be executed, for reasons of time and cost.

In coating practice (for example of car bodies), it is a common task to ascertain the effect of different coating parameters and coating processes on the color. Trials have also shown here that differences were often not detected by means of the value L at 25° geometry, but in other geometries of observation and, in particular, by means of the color coordinates a and b.

What is claimed is:

1. A method for measuring a coated test panel comprising:
   a) depositing at least one test panel in a feed station,
   b) transferring the test panel from the feed station to a measuring station by means of a gripping and moving device,
   c) moving one or more measuring devices by means of the gripping and moving device to the measuring station, carrying out one or more spatially-resolved measurements on the test panel to provide measurement data, and correlating the measurement data with a measurement location on the test panel, and
   d) transferring the measured test panel to a delivery station by means of the gripping and moving device.

2. The method of claim 1, wherein the measurement data obtained from the test panel are recorded, stored, evaluated and/or displayed electronically.

3. The method of claim 1, further comprising
   a) providing the test panels with a machine readable identifier,
   b) recording the machine-readable identifier and accepting the information contained therein into a control device of the gripping and moving device and/or a data acquisition system.

4. The method of claim 3, wherein the machine readable identifier is a barcode containing information on the desired type of measurement, the locations of the measurement and/or the identification of the test panel.

5. The method of claim 3, wherein information contained in the identifier is accepted into the control device of the gripping and moving device and determines a measuring device that is moved to the measuring station and/or at least one position on a test panel to which the measuring device is moved.

6. The method of claim 1, wherein the one or more measurements carried out on the test panel are selected from the group consisting of film thickness, leveling, color, identification of color coordinates L, a, and/or b, haze, gloss, topography, and mixtures thereof.

7. The method of claim 1, comprising carrying out the one or more measurements at various angles of observation selected from the group consisting of between 20°–80°.

8. The method of claim 7, comprising carrying out the one or more measurements at various angles of observation selected from the group consisting of 25°, 45° and 75°.

9. The method of claim 1, comprising carrying out the one or more measurements along one or more paths or area regions on the test panels.

10. The method of claim 1, wherein at least two properties are measured and are correlated with one another.

11. The method of claim 1, further comprising calibrating the one or more measuring devices using one or more standards that are moved to the measuring station by the gripping and moving device.

12. The method claim 11, comprising calibrating the one or more measuring devices by means of a reference measurement carried out using a standard instead of the test panel.

13. The method of claim 1, wherein the gripping and moving device moves the measuring device along a curved surface of the test panel to provide measurement data at a plurality of points along the curved surface.

14. The method of claim 1, wherein, in step c), a first measuring device is moved from an original position by the gripping and moving device to the measuring station and one or more test measurements are carried out on the test panel with the first measuring device, then the first measuring device is returned to its original position and at least one additional measuring device is moved from its original position by the gripping and moving device to the measuring station and one or more test measurements are carried out on the test panel with the additional measuring device, then the additional measuring device is returned to its original position.

15. An apparatus for measuring a coated test panel comprising
   a) a feed station for containing one or more test panels,
   b) a gripping and moving device for moving the test panels for measuring the test panels, c) one or more measuring devices for the measurement of coating properties of the test panels, d) a central data acquisition system that records measurement data correlated with a measurement location on the test panels, and e) a delivery station for containing one or more measured test panels.

16. The apparatus of claim 15, further comprising a reading device for the electronic reading of identifying data from the test panel.

17. The apparatus of claim 15 further comprising means for connecting one or more members selected from the group consisting of the gripping or moving device, the one or more measuring devices, the reading device, and mixtures thereof, to an electronic data processing system.

18. The apparatus of claim 15, characterized in that the feed station and/or the delivery station are designed as magazines for the test panels.

19. The apparatus of claim 15, comprising one or more measuring devices selected from the group consisting of measuring devices capable of measuring film thickness, leveling, color, haze, gloss, and mixtures thereof.

* * * * *